United States Patent
Choi et al.

(10) Patent No.: US 11,492,261 B2
(45) Date of Patent: Nov. 8, 2022

(54) METHOD OF USING CHEMICAL REACTION TRANSPARENCY OF GRAPHENE

(71) Applicant: KOREA RESEARCH INSTITUTE OF CHEMICAL TECHNOLOGY, Daejeon (KR)

(72) Inventors: Won Jin Choi, Daejeon (KR); Jeong-O Lee, Daejeon (KR); Hyunju Chang, Daejeon (KR); Ki-jeong Kong, Daejeon (KR); Ki-Seok An, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 547 days.

(21) Appl. No.: 15/532,666

(22) PCT Filed: Dec. 4, 2015

(86) PCT No.: PCT/KR2015/013234
§ 371 (c)(1),
(2) Date: Oct. 16, 2017

(87) PCT Pub. No.: WO2016/089164
PCT Pub. Date: Jun. 9, 2016

(65) Prior Publication Data
US 2018/0055976 A1  Mar. 1, 2018

(30) Foreign Application Priority Data
Dec. 5, 2014 (KR) .................. 10-2014-0174429

(51) Int. Cl.
C01B 32/186 (2017.01)
H01M 4/66 (2006.01)
(Continued)

(52) U.S. Cl.
CPC ............ *C01B 32/186* (2017.08); *A61L 27/56* (2013.01); *C01B 32/194* (2017.08); *C01B 32/23* (2017.08);
(Continued)

(58) Field of Classification Search
CPC ........ A61L 27/56; C01B 32/194; C01B 32/23; C01B 32/186; C01B 2204/20;
(Continued)

(56) References Cited

U.S. PATENT DOCUMENTS

2009/0110627 A1* 4/2009 Choi ..................... C23C 16/56
                                                        423/447.1

FOREIGN PATENT DOCUMENTS

CN    103035786 A    4/2013
KR    10-2011-0054317 A    5/2011
(Continued)

OTHER PUBLICATIONS

Gutes, et al., Graphene decoration with metal nanoparticles: Towards easy integration for sensing applications, Nanoscale 2012; 4: 438-440 (Year: 2012).*
(Continued)

*Primary Examiner* — Daniel C. McCracken
(74) *Attorney, Agent, or Firm* — Singleton Law, PLLC; Chainey P. Singleton

(57) ABSTRACT

The present invention relates to a method using chemical reaction transparency of graphene, and more specifically to a method capable of forming a desired material by a catalytic reaction on a graphene surface using the graphene which
(Continued)

inhibits oxygen diffusion without blocking electron delivery, and an applied method thereof.

6 Claims, 5 Drawing Sheets

(51) Int. Cl.
  *H01M 4/13* (2010.01)
  *H01M 4/139* (2010.01)
  *C01B 32/194* (2017.01)
  *A61L 27/56* (2006.01)
  *C01B 32/23* (2017.01)
  *H01M 4/1315* (2010.01)
  *H01M 4/86* (2006.01)

(52) U.S. Cl.
  CPC ............ *H01M 4/13* (2013.01); *H01M 4/139* (2013.01); *H01M 4/1315* (2013.01); *H01M 4/663* (2013.01); *H01M 4/8615* (2013.01); *C01B 2204/20* (2013.01); *Y02E 60/13* (2013.01)

(58) Field of Classification Search
  CPC ........ H01M 4/139; H01M 4/13; H01M 4/663; H01M 4/8615; H01M 4/1315; H01M 4/8663; Y02E 60/13; C12N 2533/32; C12N 2533/52; C12N 2533/54; C12N 5/0018; H01L 31/022425; H01G 11/36
  See application file for complete search history.

(56) References Cited

FOREIGN PATENT DOCUMENTS

| KR | 10-2011-0129528 A | 12/2011 |
| KR | 10-2013-0035894 A | 4/2013 |
| KR | 20140098714 A | 8/2014 |

OTHER PUBLICATIONS

Kim, et al., Multiply folded graphene, Physical Review B 2011; 83: 245433-1 to 245433-8 (Year: 2011).*

Wei, et al., Controllable Chemical Vapor Deposition Growth of Few Layer Graphene for Electronic Devices, Accounts of Chemical Research 2013; 46(1): 106-115 (Year: 2013).*

Gutes, Albert et al. "Graphene decoration with metal nanoparticles: Towards easy integration for sensing applications", Nonoscale, 2012 vol. 4, 438-440.

Lee, Jung Min et al., "ZnO Nanorod-Graphene Hybrid Architectures for Multifunctional Conductors", The Journal of Physical Chemistry C, 2009, vol. 113, 19134-19138.

International Search Report, PCT/KR2015/013234 [KIPO] dated May 12, 2016.

Gutes et al.; "Graphene decoration with metal nanoparticles: Towards easy integration for sensing application"; Nanoscale 2012, vol. 4, Dec. 7, 2011; pp. 438-440.

* cited by examiner

[FIG. 1]
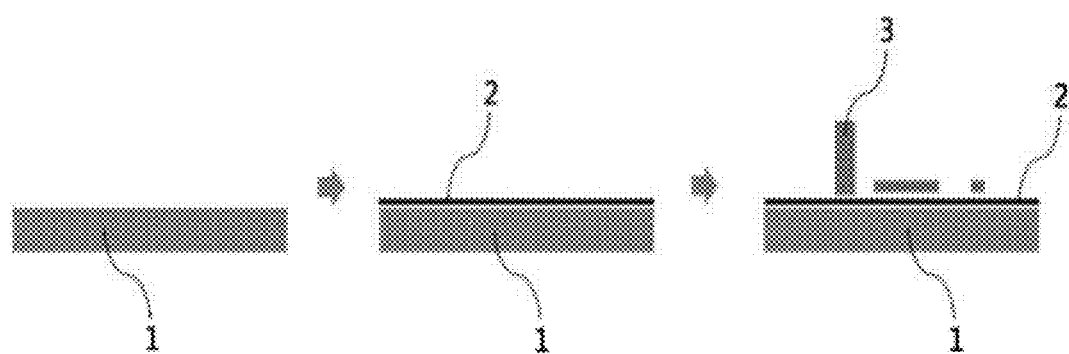

[FIG. 2]
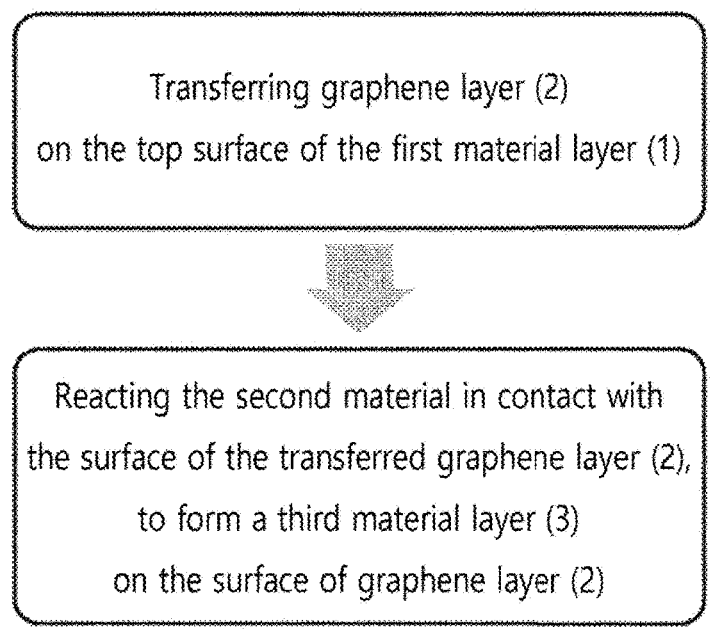
[FIG. 3]
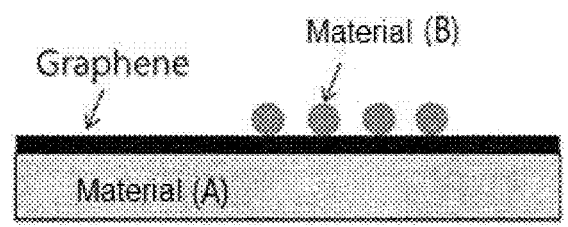
[FIG. 4]
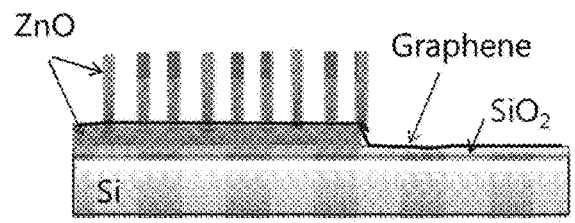

[FIG. 7]
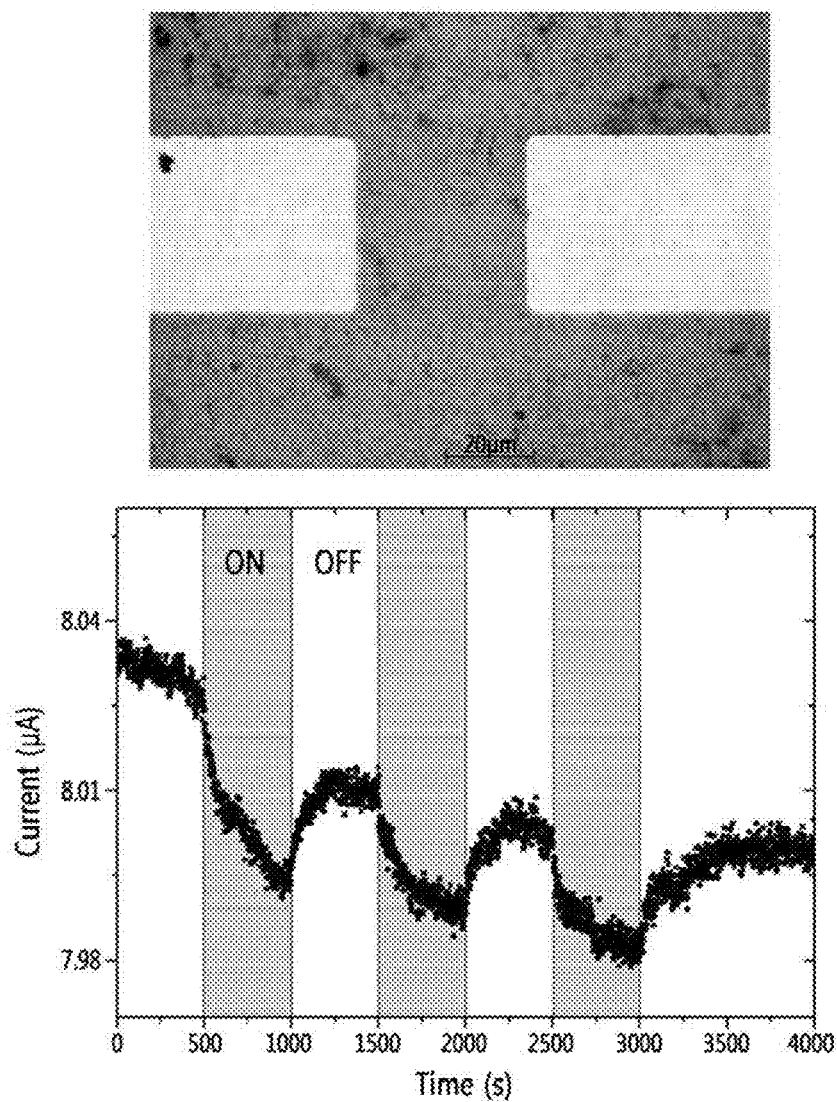
[FIG. 8]
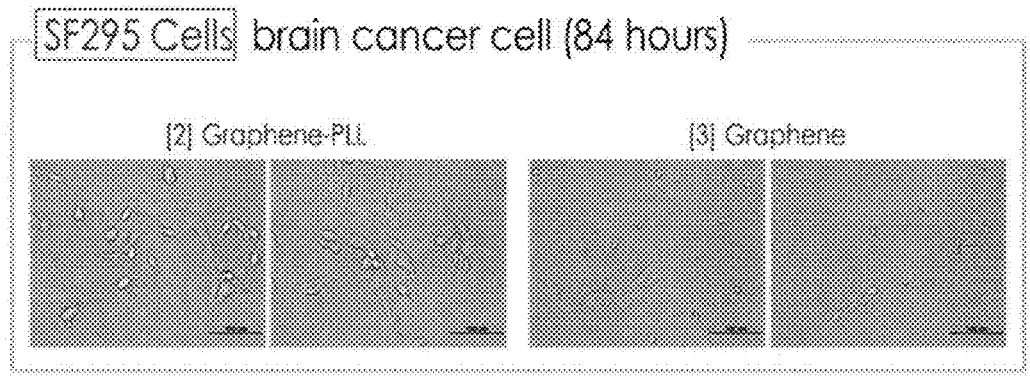

METHOD OF USING CHEMICAL REACTION TRANSPARENCY OF GRAPHENE

DETAILED DESCRIPTION

Technical Field

The present invention relates to a method of using chemical reaction transparency of graphene.

Background Art

Graphene is a transparent, single-atom-thick conductive material with carbon atoms in a hexagonal arrangement. Graphene became a Nobel Prize-winning material in 2010, as it is not only structurally and chemically stable, but it also has excellent optical, electrical, and mechanical properties. Graphene has received much attention. As graphene is a single atom-thick and an ideal two-dimensional material, it has much potential as an element with electrical, display, and energy applications.

Graphene exhibits high transmittance to visible light, and due to its flexibility, has received much attention as a transparent electrode which is flexible. The high light transmittance is based on the fact that graphene is single atom-thick, which is a very special case, and is different from light transmittance of general cases. Accordingly, many scientists have been reported proof that graphene has not only the light transparency, but also the transparency for wettability and for van der Waals forces. However, there has been no clear theory regarding the fundamentals and phenomena for the transparency of graphene. Moreover, an appropriate application using the transparency of graphene has not yet been found.

DISCLOSURE OF INVENTION

Technical Problem

An object of the present invention is to provide a method of utilizing chemical transparency of graphene; including forming various materials on graphene surface and growth of epitaxial layers on graphene using the chemical reaction transparency of graphene and an application method thereof. In particular, the present invention applies the chemical transparency of graphene to a reaction in which movement of electrons takes place, such as a redox reaction where an oxidation number of an atom changes and also to a electrostatic interaction reaction.

Technical Solution

A first aspect of the present invention provides a method of performing a catalytic reaction using chemical transparency of graphene on a substrate comprising a first layer comprising a catalyst; and a second layer comprising graphene formed on the first layer, by performing a catalytic chemical reaction at a region of the second layer where the graphene is positioned on the catalyst.

A second aspect of the present invention provides a method of preparing a surface-modified graphene through the chemical reaction on a substrate comprising a first layer comprising a catalyst; and a second layer comprising graphene formed on the first layer, comprising performing a catalytic chemical reaction at a region of the second layer where the graphene is positioned on the catalyst.

A third aspect of the present invention provides an electrode, comprising a first layer comprising an electrode active material and a second layer comprising graphene formed on the first layer, in which the electrode active material performs an oxidation-reduction reaction at a region of the second layer where the graphene is positioned on the electrode active material.

A fourth aspect of the present invention provides a cell comprising the electrode according to the third aspect.

A fifth aspect of the present invention provides a sensor, comprising a first layer comprising a catalyst; a second layer comprising graphene formed on the first layer; and metal nanoparticles formed through a catalytic chemical reaction at a region of the second layer where the graphene is positioned on the catalyst.

A sixth aspect of the present invention provides a sensor chip comprising the sensor according to the fifth aspect.

A seventh aspect of the present invention provides a cell culture substrate, comprising a first layer comprising the material inducing adhesion or proliferation of cells; and a second layer comprising graphene formed on the first layer, in which the material inducing adhesion or proliferation of cells performs the adhesion or proliferation of cells at a region of the second layer where the graphene is positioned on the material inducing adhesion or proliferation of cells.

An eighth aspect of the present invention provides a transplant comprising the cell culture substrate according to the seventh aspect.

A ninth aspect of the present invention provides a method of performing a chemical reaction of a first reactant and a second reactant in a condition where the first and second reactants, between which a chemical reaction occurs through mutual transfer of electrons and holes, are separated by graphene exhibiting chemical transparency.

A tenth aspect of the present invention provides a device, comprising a first means forming a first product from a first reactant; a second means forming a second product from a second reactant; and graphene capable of exhibiting chemical transparency and separating the first and second reactants, in which electrons or holes, which are produced when the first product is produced from the first reactant, are delivered to the second reactant through the graphene to produce the second product.

An eleventh aspect of the present invention provides a multi-layered electronic device, comprising at least one active layer between two electrode layers, wherein at least one layer of graphene exhibiting chemical transparency is inserted between layers.

Hereinafter, the present invention will be described in detail.

Graphene is a single-atom-thick conductive material with carbon atoms in a two-dimensional honeycomb lattice. Due to its high flexibility, high electric conductivity and heat dissipation properties, graphene has received much attention as a material having unlimited fields of application.

The various fields of graphene application are touch panels, flexible displays, high-efficiency solar cells, heat dissipation films, coating materials, ultra-thin speakers, sea water desalination filters, electrode for secondary cells, high-speed chargers, sensors, etc. For such applications, an additional material can be formed on the graphene surface as needed. However, graphene is chemically stable, and thus does not cause chemical reactions. Therefore, modification techniques of forming an additional material on the surface are limited. Accordingly, there has been a demand for new solutions for graphene surface modification.

In the present invention, by performing a catalytic chemical reaction on the graphene surface using the chemical reaction transparency of graphene, a method of performing a catalytic reaction which can create a desired material on the graphene surface can be provided.

Additionally, in the present invention, by transferring the graphene on a desired substrate surface of an electrode, etc., capability of the substrate surface to transfer electrons is maintained while inhibiting inactivation of the substrate surface such as by oxidation. Further, electricity conductivity can be obtained by graphene while maintaining the capability of the substrate to transfer electrons.

A crystal structure of graphene refers to bonds in hexagonal arrangements stretched in a two-dimensional direction by $sp^2$ bonds, i.e., an atomic structure in which three bonds are attached to one vertex. Consequently, a two-dimensional crystal in a widely spread honeycomb lattice and pores in a hexagonal form are formed, and this is why graphene is present in a thin film of single-atom thickness. This is the reason that graphene forms the thinnest layer which can be present in a stable molecular structure. Likewise, graphene, as a film having single-atom thickness and pores, is very transparent.

In the present invention, having single-atom thickness and pores, graphene does not hinder a chemical reaction of a material located above graphene under the influence of a material located under graphene, thereby allowing a desired chemical reaction to be performed. The present invention also found that by using such chemical reaction transparency, a desired material with a desired crystalline order can be created on the graphene surface. In other words, in the present invention, as a catalytic chemical reaction is possible at a region of the second layer where the graphene is positioned on the catalyst on a substrate comprising a lower first layer comprising a catalyst; and a upper second layer comprising graphene formed on the first layer, a catalytic reaction to which such chemical transparency of graphene is applied can be performed, and the graphene surface can be modified. Additionally, the chemical transparency of graphene can be used for an electrode, sensor, cell culture substrate, etc. The present invention is based thereon.

The method of the present invention of performing a catalytic reaction using chemical transparency of graphene can be achieved by performing a catalytic chemical reaction at a region of the second layer where the graphene is positioned on the catalyst on a substrate comprising a first layer comprising a catalyst; and a second layer comprising graphene formed on the first layer.

As an aspect of performing the catalytic reaction, the catalyst forms a catalytic pattern on the first layer, and a catalytic chemical reaction is performed on the graphene along the catalytic pattern, thereby creating a product of the chemical reaction along to the catalytic pattern.

A "catalyst" increases a rate of a thermodynamically-possible chemical reaction to reach equilibrium, and is not consumed by the reaction itself.

It is difficult to classify types of the catalysts according to one principle. Classification methods of the catalysts may include classification according to energy source (photocatalyst, electrocatalyst, etc.), classification according to catalytic material (metal catalyst, metal oxide catalyst, etc.), classification according to function of catalyst (oxidation catalyst, polymerization catalyst, hydrogenation catalyst, etc.), etc.

In the present invention, the catalyst may be a photocatalyst, electrocatalyst, or electrode active material.

The "photocatalyst" is a catalyst that absorbs light as a semiconductor and promotes an oxidation-reduction reaction. Materials which can be used as the photocatalyst are $TiO_2$ (anatase), $TiO_2$ (rutile), ZnO, CdS, $ZrO_2$, $SnO_2$, $V_2O_2$, $WO_3$, etc.; a perovskite-type complex metal oxide ($SrTiO_3$); etc. However, it is preferable that semiconductive materials that can be used in actual catalytic reactions be optically active and have no optical corrosion. It is also preferable that the semiconductive materials be biologically or chemically inactive, be capable of using UV or visible light, and be inexpensive in the economic aspect. When energy in a specific region is applied to the semiconductor, electrons are excited from the valence band to the conduction band. The electrons ($e^-$) are formed in the conduction band and holes ($h^+$) are formed in the valence band. These electrons and holes cause various reactions such as decomposition of harmful materials through strong oxidation or reduction.

The "electrocatalyst" is a catalyst that promotes a catalytic reaction by an electrochemical effect. A semiconductor-producing technology such as CVD (chemical vapor deposition), a process of producing chloride using a catalyst coated with thin ruthenium oxide film, etc. are examples thereof.

The "active electrode material" or "electrode active material" is a material providing or improving functions of an electrode. For example, an active electrode material of a double-layer capacitor electrode includes particles having high porosity. Non-limiting examples of the active electrode material are activated carbon, carbon nanotube (CNT), vapor grown carbon fiber (VDCF), carbon aerogel, carbon nanofiber (CNF) produced by carbonizing a hydrocarbon or fluorinated hydrocarbon polymer, graphite, metal, metal oxide, alloy, or a combination thereof. Additionally, as an active electrode material in a lithium secondary battery, there are a cathode active material used for a cathode and an anode active material used for an anode. Representative cathode active materials are $LiCoO_2$, $LiNi_{1/3}Co_{1/3}Mn_{1/3}O_2$, $LiNi_{0.5}Co_{0.3}Mn_{0.2}O_2$, $LiMn_2O_4$, and $LiFePO_4$, and an anode active material can be lithium metal or a material which can intercalate or deintercalate a lithium ion.

In the present invention, the catalyst can be a metal, metalloid, semi-conductor, metal oxide, or an oxide of the metalloid.

In the present invention, the catalyst may act as a reducing agent in the chemical reaction. In other words, the catalyst in the present invention can function as an electron donor. Accordingly, the catalyst of the present invention allows a metal in a form of an ion to be precipitated in a form of a metal nanoparticle, or functions itself as a seed, thereby continuously forming the same materials on the catalyst surface to form a structure in a form of a rod.

In the present invention, the catalyst can be used as a catalyst of any one reaction of hydrogenation, dehydrogenation, dehydrocyclization, dehydration, hydration, isomerization, decomposition, hydrogenolysis, alkylation, polymerization, oxidation, ammonia oxidation, oxidative chlorination, and disproportionation.

Types of the catalysts, and examples of reactions in which such catalysts can be used are summarized in Table 1 below.

TABLE 1

| Reaction | Type of catalyst | Examples |
| --- | --- | --- |
| Hydrogenation | Noble metal, transition metal, and metal oxide | Acetylene hydrogenation, MAPD, C4 selective hydrogenation, C5 selective hydrogenation, PGHT, CH unit, solvent, hydrogenation unit, etc. |

TABLE 1-continued

| Reaction | Type of catalyst | Examples |
|---|---|---|
| Dehydrogenation | Noble metal, transition metal, and metal oxide | Preparing olefin using paraffin (propane/C4 LPG dehydrogenation, etc.), prepare an aldehyde from an alcohol |
| Dehydrocyclization | Noble metal, transition metal, and metal oxide | Preparing an aromatic compound from paraffin or olefin |
| Dehydration | Acidic compound | Synthesizing an ether and olefin from an alcohol |
| Hydration | Acid and oxide | Preparing an alcohol from olefin |
| Isomerization | Acid/base/metal catalyst | Preparing i-paraffin from n-paraffin, pX from mX, etc. |
| Decomposition | Acid catalyst | FCC |
| Hydrogenolysis | Metal-supported acid catalyst | Hydrogenation of oil |
| Alkylation | Acid catalyst | Olefin + Paraffin → i-Paraffin, Aromatic + Olefin → Alkyl Aromatic |
| Polymerization | Acid, base, acid oxide, Friedel Craft type | Polymerization of olefin (PEPP) |
| Oxidation | Oxide | EO, PO, acrylolein, SO3 |
| Ammonia oxidation | Complex oxide | Sohio process |
| Oxidative chlorination | Metal chloride | VCM |
| Disproportionation | Solid acid | Tatoray |

In an exemplary embodiment of the present invention, Ge, Al, $SiO_2$, Si, GaAs, Cu, or ZnO was used as the catalyst.

In the present invention, the second layer inhibits inactivation of the catalyst. In the present invention, the second layer, as a layer comprising graphene, is located on the first layer comprising a catalyst where it can inhibit the inactivation of the catalyst.

Generally, a metal catalyst is inactivated by poisoning, fouling, sintering oxidation, etc.

Poisoning refers to a phenomenon in which products or other impurities are strongly adsorbed onto a metal surface which is an active point of the reaction to lower an activity of a catalyst. Examples of such chemical species are VA group (N, P, As, and Pb), VIA group (O, S, Se, and Te), harmful heavy metals and ions (Pb, Hg, Bi, Zn, Cd, Cu, Fe, etc.), molecules having an unsaturated electron structure (CO, NO, and benzene), etc.

Fouling is a physical phenomenon in which carbons, etc. are accumulated on a metal surface or in pores, thereby reducing an activity of a catalyst, and accumulated carbons can be burned at a high temperature by steam, etc., and the metal can be regenerated. The accumulated carbons can be formed in various forms such as carbide, polymer, and graphite, according to a reaction condition. In this regard, an inactivated form can vary.

Sintering refers to a phenomenon in which small metal crystals or atoms move, and thus a size of a catalyst metal particle increases, thereby decreasing a surface area of the metal. For example, a catalyst for purification of automobile exhaust gas loses 95% of initial reaction activity by sintering during 50,000 miles of driving. A degree of sintering significantly varies according to temperature, types of metal and support thereof, and atmosphere, and a mechanism of sintering is explained in terms of crystallite migration and atom migration.

Additionally, there are cases in which a catalyst metal becomes a volatile material such as a particular carbonyl compound, oxide, sulfide, and halide and is consumed in a reaction condition in which CO, NO, hydrogen, $H_2S$, halogen, etc. are included, thereby reducing reaction activity. Formation of nickel carbonyl or iron carbonyl in an atmosphere of carbon monoxide, and $RuO_3$, PbO, and $MoS_2$ formation at room temperature, a temperature of 850° C. or above, and 550° C. or above, respectively, are examples thereof.

In the present invention, the method of preparing the surface-modified graphene using the chemical reaction transparency of graphene may include performing a catalytic chemical reaction at a region of the second layer where the graphene is positioned on the catalyst in a substrate comprising a first layer comprising a catalyst; and a second layer comprising graphene formed on the first layer.

As an aspect of the method of preparing the surface-modified graphene, a method in which the first layer forms a catalyst pattern using the above catalyst, and the chemical reaction is performed at a region of the second layer where the graphene is positioned on the catalyst, thereby preparing the surface-modified graphene along the catalyst pattern, can be provided.

An aspect of the preparation method of the surface-modified graphene of the present invention, as shown in FIGS. 1 and 2, may include transferring the second layer (2) comprising graphene on the first layer (1) comprising the catalyst (step 1); and reacting a material, which is capable of reacting with the catalyst, in contact with the transferred the second layer (2) comprising graphene to form a product (3) on the surface of the graphene layer (step 2).

The graphene transfer can be performed using a conventional graphene transfer method. As representative examples, there are a transfer method using a polymer for graphene support, heat-release tape, or roll; a method using static electricity; an electrochemical lamination method; etc.

In the present invention, as the graphene-transfer method, a transfer method using a polymer for graphene support can be preferably used.

Preferably, step 1 may include the following steps:

positioning graphene on a substrate to obtain the second layer comprising graphene (step a);

coating a polymer for graphene support on the second layer comprising graphene (step b);

separating the polymer-coated second layer comprising graphene from the substrate (step c);

transferring the polymer-coated second layer comprising graphene on the surface of the first layer comprising the catalyst (step d); and removing the polymer from the transferred graphene second layer (step e).

In the present invention, any substrate can be used as long as it is a flat support capable of forming a second layer comprising graphene. Specifically, the substrate may be a transition metal foil, or a substrate in which a transition metal layer is deposited on a layer consisting of silicon, silicon oxide, or a combination thereof, but is not limited thereto. The transition metal foil may include transition metals such as Cu, Ni, and Pt, which are capable of adsorbing carbon and inducing graphene formation.

In the present invention, in step a, it is preferable that the second layer comprising graphene be laminated as a one-atom layer. When the second layer comprising graphene is laminated as a one-atom layer, it can have one-atom thickness.

In the present invention, the positioning of graphene can be performed using chemical vapor deposition, but is not limited thereto.

Chemical vapor deposition allows large-scale growth and mass production of graphene. It is a method of synthesizing graphene using as a catalyst for graphene synthesis a transition metal which is capable of forming carbon or an alloy at a high temperature or has excellent adsorbability to carbon. Specifically, a transition metal layer such as a Cu, Ni, or Pt layer, that is, a graphene-synthesizing catalyst layer which adsorbs carbon well, or a layer in which the transition metal layer is deposited as a graphene-synthesizing catalyst layer on a $SiO_2/Si$ substrate can be used as a substrate. Carbon reacts with the graphene-synthesizing catalyst layer so that an appropriate amount of carbon is dissolved into or adsorbed onto the catalyst layer, at a high temperature of 1000° C. in a mixed gas atmosphere of methane, hydrogen, etc. By cooling afterwards, the carbon atoms included in the graphene-synthesizing catalyst layer are crystallized on the surface, thereby forming a graphene crystal structure, to form a second layer comprising graphene. By removing the graphene-synthesizing catalyst layer, the synthesized graphene-containing second layer is separated from the substrate and can be used according to a desired purpose of use.

In the present invention, the polymer for graphene support may be polymethyl methacrylate (PMMA), polydimethylsiloxane (PDMS), or a combination thereof, but is not limited thereto.

In the present invention, the coating of step b can be performed with spin coating or drop coating.

In the present invention, step c can be performed by etching the substrate. Specifically, in a case where the substrate is copper foil, the substrate can be etched using a copper etching solution. A commercially available copper etching solution can be used.

In the present invention, step e can be performed by dissolving the polymer for graphene support. Specifically, by dissolving the polymer for graphene support with a solvent such as acetone, etc., the polymer can be removed from the graphene layer.

In the present invention, an additional support layer may be the first layer.

In the present invention, the support layer may consist of materials which are not involved in a chemical reaction of the first layer by a catalyst, or the support layer may be a metal (Example 5).

As an aspect of the present invention, as shown in FIG. 3, a layered structure including a first layer comprising a catalyst (material A), a second layer comprising graphene formed on the first layer, and a product (material B) formed on the second layer by a catalytic reaction may be provided (FIG. 3).

As another aspect of the present invention, as shown in FIG. 4, a layered structure including a support layer; a first layer including a catalyst formed on the support layer; a second layer comprising graphene formed on the first layer; and a product of a catalytic reaction formed on the second layer comprising graphene may be provided (FIG. 4).

Specifically, the layered structure shown in FIG. 4 may include a support layer ($SiO_2/Si$), first layer comprising a patterned catalyst (ZnO) on the support layer, a second layer comprising graphene formed on the first layer, and a product (ZnO) of a catalytic reaction formed on the second layer comprising graphene. The layered structure shown in FIG. 4, by using a support layer consisting of materials which are not involved in a catalytic reaction, generates a product of the catalytic reaction only at a region of the second layer comprising graphene, which corresponds to the catalyst pattern of the first layer, thereby forming a product of the catalytic reaction in the pattern same as that of the first layer.

Meanwhile, the present inventors found that according to its metal oxidation state, a metal oxide induces or changes an interaction (e.g., polymer adsorption) on the graphene adjacent thereto. For example, the present inventors found that an oxidation state of the copper surface below graphene plays an essential role in binding PMMA to the graphene. In other words, a copper oxide, particularly $Cu^{II}$, can induce polymer adsorption according to its oxidation state. $Cu^{I}$ has little influence on the surface energy of graphene. Additionally, the present inventors found that an oxidation state of a metal-containing layer below graphene can control the upper surface energy of the graphene. Accordingly, to modify the graphene with polymer, a metal oxidation state of the layer which contains a metal capable of inducing or changing an interaction between the graphene and a corresponding polymer can be determined considering a change of the surface energy of an upper graphene thin layer on the metal-containing layer according to its oxidation state, in particular, an increase in the surface energy.

Additionally, the present invention can provide an electrode in which chemical reaction transparency of graphene is used. The electrode, comprising a first layer comprising an electrode active material and a second layer comprising graphene formed on the first layer, can perform an oxidation-reduction reaction by the electrode active material at a region of the second layer where the graphene is positioned on the electrode active material.

Additionally, the present inventor can provide a cell comprising the electrode. The cell may be any one of a primary cell, a secondary cell, a supercapacitor, a fuel cell, and a solar cell.

When a metal is exposed to an atmospheric environment including air and water, an oxide layer or metal hydroxide is formed on the metal surface. A metal chloride may be formed thereon as well. As described, a thin metal oxide or metal hydroxide layer naturally formed on a metal surface in an atmospheric environment prevents further oxidation or corrosion of the metal surface. However, as the layer is very thin, it is fundamentally weak, and a crack may lead to deeper corrosion.

As most metal oxides or metal hydroxides are nonconductors or semiconductors, they have poor conductivity. Accordingly, when a metal is used as an electrode, they become a factor which increases contact resistance. When a metal is used as an electrode, the metal oxide or metal hydroxide layer becomes a region where scattering of electron transfer takes place and a factor which cannot maintain a spin property of electrons.

Many electronic devices, which use a metal as an electrode, use gold as an electrode, as the gold barely forms an oxide layer or hydroxide layer, or use a metal in process without exposing the metal to air or water. However, these methods are accompanied by many limitations in terms of cost and applications.

Therefore, if graphene is formed on a metal surface according to the present invention, graphene not only acts as a layer capable of preventing oxidation and corrosion of the metal, but also reduces contact resistance of the metal and maintains the spin property of an electron, thereby improving applicability to the electronic devices.

For example, nickel, as a magnetic metal, can be used as an electrode of a spintronic device which applies a magnetic property of an electron to an electronic device. Nickel oxide and nickel hydroxide on the nickel surface have hindered use of nickel as an electrode element. However, by forming graphene on the metal surface, graphene can not only act as a protective layer which can solve the problem, but also help the nickel play its role as an electrode by chemical transparency of graphene.

A primary cell refers to a disposable battery which has to be discarded after a single use, as an electrochemical reaction within the cell is irreversible. Contrary to secondary cell which can be recharged and reused, it is impossible for the primary cell to reverse chemical reactions occurred during discharge by applying a current to inside the cell. Chemical reactants (e.g., atoms such as lithium in a lithium battery) do not return to their original position even if a reverse current is applied. Accordingly, capacity of the battery will not recover. The primary cell dies when either cathode or anode, or both are wasted.

A secondary battery or secondary cell is a type of an electrical battery which can refer to a rechargeable battery or storage battery. It contains at least one electrochemical cell, and is a form of an energy accumulator for electrochemical energy storage. As an electrochemical reaction that occurs therein is electrically reversible, it is called a secondary cell. The secondary cell has a very wide variety of sizes and forms ranging from a coin cell to a megawatt system connected for stabilizing a power distribution network. Each different combination of compounds including lead-acid, NiCd, NiMH, Li-ion, and Li-ion polymer is widely used. Additionally, there is a redox flow battery as another example of the secondary battery. Non-limiting examples of the redox flow battery may include all-vanadium redox flow battery having V(IV)/V(V) redox couple as a cathode electrolyte and V(II)/V(III) redox couple as an anode electrolyte; vanadium redox flow battery having halogen redox couple as a cathode electrolyte and V(II)/V(III) redox couple as an anode electrolyte; polysulfide bromine redox flow battery having halogen redox couple as a cathode electrolyte and sulfide redox couple as an anode electrolyte, and Zn—Br redox flow battery having halogen redox couple as a cathode electrolyte and zinc redox couple as an anode electrolyte.

A supercapacitor or ultracapacitor is also known as electric double-layer capacitor, and may be a general term referring to an electrochemical capacitor. Contrary to a nanoscale dielectric capacitor having a high value of capacitance, the supercapacitor does not include a conventional solid dielectric. A capacitance value of an electrochemical capacitor is determined based on two storage principles, that is, double-layer capacitance and pseudocapacitance indivisibly contributing to a total capacitance. The supercapacitor consists of two electrodes separated by an ion permeable membrane (i.e., separator) and an electrolyte which electrically connect the two electrodes. When an electrode is polarized by applying voltage, ions within the electrolytes create electric double layers of polarity opposite to that of the electrode. For example, a positively polarized electrode obtains an anion layer along with a charge-balance layer of a cation adsorbed onto a negative charge layer on an electrode/electrolyte interface. In a case where an electrode is negatively polarized, the opposite phenomenon takes place.

A fuel cell is a device that generates electric energy by electrochemically reacting an oxidizing agent and fuel. The electrochemical reaction can generate energy continuously as long as fuel is continuously supplied. Other batteries chemically store electric energy in a closed system, whereas the fuel battery generates electric power by consuming the fuel. Additionally, electrodes of other batteries changes through a reaction according to their charging/discharging state, but those of the fuel cell act as a catalyst, and thus are relatively stable. Various materials can be used as the fuel and the oxidizing agent. Hydrogen fuel cell uses hydrogen as fuel and oxygen as an oxidizing agent. Additionally, hydrocarbon, alcohol, etc. can be used as fuel, and air, chloride, chlorine dioxide, etc. can be used as an oxidizing agent.

Solar cell or photo cell means a device capable of converting solar energy to electric energy. When light having energy greater than a band-gap energy is irradiated in a semiconductor junction having a PN junction face, electrons and holes are formed. An interior electric field created in the junction area moves thus-formed electrons and holes to an N-type semiconductor and a P-type semiconductor, respectively, to create an electromotive force. The electrodes attached each to the N- and P-type semiconductors become an anode and a cathode, enabling application of direct current. As a material for solar cell semiconductor, not only silicon, but also gallium arsenide, cadmium telluride, cadmium sulfide, indium phosphide, or a complex thereof is used, but silicon is generally used.

An electrode of a battery or capacitor may be a form of thin film coating including an electrode active material which is applied and electrically connected to a conductive metal current collector. It is preferable that the electrode has not only excellent conductivity, but also long-term chemical inertness, high resistance to corrosion, and surface area per unit volume and mass. Above all, it is important that the electrode can provide a large electrode surface area for excellent performance. Accordingly, a porous and spongy material specially having a high specific surface area such as activated carbon can be used. For example, by using powder having a small particle diameter as an electrode active material and applying the powder to the current collector to prepare the same in a form of a porous electrode, the electrode surface area can be rapidly increased. In the case of an active material having low electronic conductivity including contact resistance, resistance increases and potential distribution is created during charging and discharging of the battery, thereby possibly lowering utilization of the powder active material. In order to prevent this, a carbon material, etc. can be added as a conducting agent. Further, for stable application of the powder, a polymer can be used as a binder (binding agent).

Additionally, the present invention can provide a sensor using the chemical reaction transparency of graphene. The sensor may comprise a first layer comprising a catalyst; a second layer comprising graphene formed on the first layer; and metal nanoparticles formed through a catalytic chemical reaction at a region of the second layer where the graphene is positioned on the catalyst.

In the present invention, graphene, metal nanoparticles formed by a catalytic chemical reaction may form a sort of a complex, and a sensor effect of the complex of graphene and metal may be exhibited.

In the present invention, the sensor may be a gas sensor, a glucose sensor, or a surface plasmon resonance (SPR) sensor, but is not limited thereto.

A "gas sensor" may be an element which detects a particular gas component and convert the gas into an appropriate electric signal according to gas concentration. Due to having a very thin (single layer=0.3 nm) channel where electrons move, graphene has a feature that other molecular materials are easily attached to the graphene surface, thereby changing a Fermi energy level easily. Using the feature, an application of graphene as a chemical molecular gas sensor is practicable. In other words, according to the feature of the molecules attached to the graphene surface of either donating or attracting an electron, a change, i.e., increase or decrease, in conductivity of the graphene compared to an initial state can be observed. This enables production of a gas sensor which confirms the presence of molecular gases (FIG. 7).

Specifically, the gas sensor can detect at least one of hydrogen, $H_2S$, acetone, $NH_3$, toluene, pentane, isoprene, and NO, but is not limited thereto as long as the gas is detected by the complex of graphene and metal.

A "glucose sensor" may be an element which detects a redox reaction of glucose and convert the glucose into an appropriate electric signal according to glucose concentration. Most glucose sensors are based on glucose oxidase (GOD). A principle of general glucose sensors is as follows, and the sensor measures a hydrogen ion.

$$Glucose + GOD\text{-}FAD \rightarrow Gluconolactone + GOD\text{-}FADH_2$$

$$FADH_2 \leftrightarrow FAD + 2H^+ + 2e^-$$

As a noble metal provides biocompatibility and a stabilization effect which prevents a phenomenon such as dissolution of the metal during reduction, a glucose sensor based on such noble metal can provide effective selectivity and high sensitivity in a glucose reaction. Additionally, in a case of applying using noble metal nanoparticles to the graphene sensor, high biocompatibility and excellent compatibility of a biological element with an electrode may be obtained. Specifically, in a case of preparing a graphene-Au complex and a graphene-Pt complex and using the complexes as a biosensor, a stable biosensor exhibiting a high sensitivity value can be prepared. Additionally, in a case where palladium nanoparticles and graphene are applied to the glucose sensor, a sensitivity level may about 31 $\mu A/mM \cdot cm^2$ and may show high electrical conductivity in a glucose concentration range of 0.1 $\mu M$ to 1.0 mM.

A "surface plasmon resonance sensor" may be a sensor for detection using surface plasmon resonance.

A surface plasmon is a collective charge density oscillation that takes place on a surface of a thin-layer metal. A thus-generated surface plasmon wave is a surface electromagnetic wave that propagates along a metal-dielectric interface. As a metal exhibiting such phenomenon, metals such as gold, platinum, silver, copper, aluminum, etc., which release an electron easily by an external stimulus and have a negative dielectric constant are mostly used. Among the mentioned metals, silver, showing the sharpest SPR peak, and gold, showing excellent surface stability, are generally used.

An excitation of the surface plasmon induces a surface charge by discontinuity of a vertical component of an electric field at an interface of two media when the electric field is applied to the interface of the two media having different dielectric constants, that is, metal-dielectric interface, and the oscillation of the surface charges appears as a surface plasmon wave. In contrast to the electromagnetic wave in free space, the surface plasmon wave is a wave oscillating parallel to an incident plane and has a polarizing component of p-polarization. Accordingly, the excitation of the surface plasmon using an optical method can be performed by a TM-polarized electromagnetic wave.

A TM-polarized incident wave is totally reflected at an interface of a thin metal film, and an evanescent field exponentially dissipates into the thin metal film. However, at a particular incident angle and thickness of the thin film, resonance occurs when a phase of the incident wave having a direction parallel to the interface and that of the surface plasmon wave propagating along the thin metal layer-air interface coincide. The energy of the incident wave is all absorbed into the thin metal layer, and thus a reflected wave disappears. Distribution of an electric field in a direction perpendicular to the interface is exponential, and is the largest at the interface and rapidly decreases toward the thin metal layer. This is surface plasmon resonance. An angle at which reflection of incident light rapidly decreases is called a surface plasmon resonance angle.

The surface plasmon resonance angle at which surface plasmon resonance occurs, i.e., an angle at which reflected light is minimized, changes when mass or structure of dielectric on the thin metal surface layer increases or changes, respectively, consequently changing effective refractive index. Accordingly, by using the SPR principle which enables measuring such change of a material by a optical method, a biochemical reaction such as selective binding and selective separation between various biochemical materials can be detected by a change in the surface plasmon resonance angle through an appropriate chemical modification on the thin metal surface layer. Therefore, the SPR sensor can be used as a highly sensitive biochemical sensor. In the case of commercialized available BIAcore SPR sensor, 0.001 change in refractive index of a dielectric layer causes 0.10 change of the surface plasmon resonance angle, and this is known to correspond to a mass change of about 1 ng per mm unit surface area. Information on refractive index, absorption coefficient, and thickness of a sample having a multi-layered film can also be obtained through numerical analysis using the Fresnel equation.

Additionally, the present invention can provide a sensor chip which includes the sensor. It is preferable that the sensor chip be in the form of a film.

The present invention can provide a cell culture substrate using the chemical reaction transparency of graphene. The cell culture substrate, comprising a first layer comprising a material inducing adhesion or proliferation of cells; and a second layer comprising graphene formed on the first layer, may have adhesion or proliferation of cells at a region of the second layer where the graphene is positioned on the material, inducing adhesion or proliferation of cells performed by the material inducing adhesion or proliferation of cells.

In the present invention, the first layer may be produced with a metal, biocompatible polymer, biodegradable polymer, or a combination thereof, but is not limited thereto. The cell culture substrate of the present invention includes the material inducing adhesion or proliferation of cells. Even if the first layer is made of a metal, the cells are not in direct contact with the metal, as the second layer comprising graphene is positioned on the first layer, thereby inducing cell growth by the material inducing adhesion or proliferation of cells in an environment more suitable to cells.

Non-limiting examples of the biodegradable polymers are polylactic acid, polyglycolic acid, poly(lactic-co-glycolic acid), polyethylene glycol, polytrimethylene carbonate, polycaprolactone, polydioxanone, etc. Those of non-biodegradable polymers are polymethyl methacrylate, polyethylene, polytetrafluoroethylene, polyvinyl chloride, polydimethylsiloxane, polyurethane, etc.

The biocompatible polymer may be a biodegradable polymer, a non-biodegradable polymer, a copolymer thereof, or a blend in which at least two types of polymers are mixed. In other words, the biocompatible polymer may be polylactic acid, polyglycolic acid, poly(lactic-co-glycolic acid), polyethylene glycol, polytrimethylene carbonate, polycaprolactone, polydioxanone, polymethyl methacrylate, polyethylene, polytetrafluoroethylene, polyvinyl chloride, polydimethylsiloxane, polyurethane, or at least one selected from copolymers thereof, but is not limited thereto.

In the present invention, the material inducing adhesion or proliferation of cells may be extracellular matrix protein including laminin, collagen, fibronectin, etc.; poly-D/L-lysine; etc., but is not limited thereto. The material inducing adhesion or proliferation of cells may enable easy adhesion of a particular cell such as neurons and stem cells (e.g., embryonic stem cell, neural stem cell, etc.).

Cell culture is generally performed by adding a cell to be cultured with a culture medium which contains a nutrient, a growth factor, and other additives necessary for growth, proliferation, and differentiation of the cell in a cell culture container under an appropriate temperature, atmosphere, and humidity.

The cell culture substrate of the present invention may include a medium. The medium can sufficiently supply nutrients necessary for culturing bacteria, cells, plants, etc., and control osmotic pressure, pH, etc., thereby promoting cell culture. As types of the medium may differ according to a cell to be cultured, the medium of the present invention is not limited to a particular medium, and thus, a commercially available medium or a self-prepared medium can be used.

It is preferable that the cell culture substrate of the present invention may be positioned in a container having a wall to contain cells and a medium for the cell culture, or the substrate itself can be in the form of a container. For example, the cell culture substrate of the present invention may be prepared on the floor of the container, which is surrounded by the wall, by forming a first layer comprising a material inducing adhesion or proliferation of cells; and a second layer comprising graphene formed on the first layer.

The cell culture substrate may be a substrate comprising a first layer including the material inducing adhesion or proliferation of cells and a second layer formed on the first layer itself, or a substrate coated with the first and second layers. Accordingly, the substrate consisting of the first and second layers can be used as the cell culture substrate, another substrate coated with the first and second layers can be used as the cell culture substrate. In a case of the other substrate on which the first and second layers are coated, the first and second layers can be applied to a substrate conventionally used for cell culture such as a Petri dish, plate, incubator, culture bag, film, fiber, microcarrier, beads, etc., or other substrates or transplants that can be used for cell culture, but is not limited thereto.

The cell culture substrate of the present invention can be present in any form as long as a cell can be cultured on the second layer surface of the substrate comprising a first layer including a material inducing adhesion or proliferation of cells; and a second layer comprising graphene formed on the first layer. For example, the cell culture substrate of the present invention itself can be a container, a transplant, or part of the container or the transplant. Additionally, the cell culture substrate of the present invention is not limited with respect to a size, shape, material, color, volume, etc. other than the form.

A type of cells that can be cultured on the cell culture substrate according to the present invention is not particularly limited. Specifically, the cell culture substrate of the present invention can be widely used for culturing animal cells, in particular, adherent cells such as fibroblasts, smooth muscle cells, vascular endothelial cells, corneal cells, chondrocytes, stromal cells, small intestinal epithelial cells, epidermal keratinocytes, osteoblasts, bone marrow mesenchymal cells, embryonic stem cells, adult stem cells, neural stem cells, nerve cells, glial cells, tumor cells, etc., and can be also used for culturing floating cells such as blood cells, etc.

Additionally, the cell culture substrate according to the present invention can be used for bacteria culture. Non-limiting examples of the bacteria include cocci including coccus, diplococcic, streptococci, staphylococci, sarcina, and tetrad; bacilli including coccobacillus, diplobacilli, palisades, *Streptobacillus, fusiform bacillus*, and comma shaped bacillus; *spirilla* including *Borellia, bibrio, Spirochete, and Reptospirra*; and other bacteria including *Helicobacter, Vibrio, Bdellovibrio,* and *Corynebacteriaceae*.

The cell culture substrate according to the present invention may further include a cell culture material for cell culture coated on the surface of the substrate including a first layer comprising a material inducing adhesion or proliferation of cells; and a second layer comprising graphene formed on the first layer.

A specific example of a method of coating the cell culture material may comprise sterilizing a substrate comprising the first and second layers according to the present invention; soaking the substrate having the sterilized first and second layers in a cell culture medium containing a biocompatible material such as protein such as serum or albumin, growth factor, and antibody, which is engaged in cell culture; etc.; and incubating the substrate in a carbon dioxide incubator.

The sterilization of the substrate having the first and second layers formed thereon can be performed by a conventional sterilization method in the art (step (a)). As an example, the sterilization can be performed by soaking in an alcohol for a certain amount of time, preferably soaking in ethanol for at least one hour, but is not limited thereto. Afterwards, step (a) may further include removing remaining alcohol solution, e.g., washing off with phosphate buffered saline (PBS) at least twice, but is not limited thereto.

The serum coated on the surface of the substrate having the sterilized first and second layers may be fetal bovine serum (FBS), but is not limited thereto. Additionally, the cell culture medium may contain the serum preferably in an amount of 5 to 20 wt %, more preferably 10 wt %, but is not limited thereto.

It is preferable that the cell culture medium may include a material inducing cell movement, such as a material inducing differentiation of a stem cell into a particular cell, a material inducing epithelial mesenchymal transition (EMT), etc. Specific examples thereof may include an organic compound, polymer, peptide, protein, polynucleotide, genes such as DNA, RNA, etc. For example, a culture medium to which the materials are further added, or a culture medium including a material secreted from a cultured cell obtained by removing the cell after culturing the particular cell in a culture medium including serum can be used, but it is not limited thereto.

Specifically, as the material inducing differentiation of a stem cell into a particular cell varies according to a type of the stem cell and that of the particular cell which are differentiated, the material is not limited as long as it is known to induce cell differentiation in the art.

Meanwhile, the substrate having the first and second layers, which are soaked in the cell culture medium, can be coated with a material for cell culture by culturing the substrate having the first and second layers in a $CO_2$ incubator. It is preferable that the incubation can be performed at least 12 hours in the incubator, but is not limited thereto. As the thus-produced cell culture substrate is coated with the material for cell culture, which enables adhesive culture of cells, the cell culture substrate can be efficiently used in cell culture.

Additionally, the present invention can provide a transplant including a first layer comprising a material inducing adhesion or proliferation of cells; and a second layer comprising graphene formed on the first layer according to the present invention.

"Transplant", as a support isolating a damaged area from outside or enabling a transplanted cell or secreted therapeutic material to stay, is a material which can be transplanted to a human body or mammalian animal. Such transplant is a tissue-engineering support, and unlimitedly includes a metal, a synthesized polymer having biodegradability, a natural material, and other various materials used in the art.

Even in case of using a first layer of a metal material, the transplant of the present invention has the second layer comprising graphene formed on the first layer, disabling a direct contact of the metal surface with in vivo cells, and has adhesion and proliferation of cells effectively induced by a material inducing adhesion or proliferation of cells of the first layer, and thus can be useful in metal material application.

It is preferable that the transplant according to the present invention can be prepared by eliminating irritation and/or discomfort when implanted, and coating a flexible substrate with first and second layers to enable free and natural movement.

Additionally, to improve adhesion and growth of cells, the second layer of the cell culture substrate according to the present invention may be further coated with serum.

In the present invention, the transplant may be used for regeneration of bone or teeth, but is not limited thereto.

In the present invention, the transplant may be a transplant in which a target material in a form of an organic compound, polymer, protein, peptide, DNA, RNA, or polynucleotide, capable of inducing differentiation of a stem cell into a particular cell or cell movement toward a particular direction is coated on the second layer of the cell culture substrate.

Additionally, the present invention can provide a method of performing a chemical reaction using chemical reaction transparency of graphene.

As an example, the present invention can provide a method of performing a chemical reaction of a first reactant and a second reactant in a condition where the first and second reactants, between which a chemical reaction occurs through mutual transfer of electrons and holes, are separated by graphene exhibiting chemical transparency.

In the present invention, the chemical reaction may be a redox reaction, but is not limited thereto.

A redox reaction, or reduction-oxidation, is a chemical reaction in which an oxidation state of an atom changes. Oxidation and reduction are opposite actions, and when oxidation occurs in one material, reduction occurs on the opposite material. Oxidation means that a molecule, atom, or ion gains oxygen or "loses" hydrogen or electron. Reduction means that a molecule, atom, or ion loses oxygen or "gains" hydrogen or electron.

In the present invention, the first reactant is oxidized, and the second reactant is reduced in a condition of being separated by graphene, thereby a chemical reaction of the first and second reactants takes place.

Additionally, the present invention can provide a device performing a chemical reaction using chemical reaction transparency of graphene.

As an example, the present invention can provide a device, comprising a first means forming a first product from a first reactant; a second means forming a second product from a second reactant; and graphene capable of exhibiting chemical transparency and separating the first and second reactants, in which electrons or holes, which are produced when the first product is produced from the first reactant, are delivered to the second reactant through the graphene to produce the second product.

The device may be an electronic device, but is not limited thereto as chemical reaction transparency of graphene is exhibited even in a device which does not include an electrode.

As previously described, the present invention can provide an electronic device using chemical reaction transparency of graphene. The electronic device is a multi-layered electronic device, comprising at least one active layer between two electrode layers, wherein at least one layer of graphene exhibiting chemical transparency is inserted between layers.

Graphene inserted between two layers maintains capability of the substrate surface to transfer electrons, while inhibiting inactivation of the substrate surface such as oxidation, and also maintains a function and/or capability of each layer where graphene is inserted, while acting as a protective layer.

Accordingly, graphene can be inserted between layers in an electronic device having a multi-layered structure including two electrodes (e.g., organic light-emitting device, solar cell, secondary cell, and capacitor), preferably an organic electronic device, as needed. For example, an organic electroluminescent device has a structure in which one or more organic layers are between cathode (electron injection electrode) and anode (hole injection electrode). As the organic layer, a hole injection layer (HIL), hole transport layer (HTL), electron transport layer (En), electron injection layer (EIL) can be included in addition to a light emitting layer (EML). Considering luminescent property of the light emitting layer, an electron blocking layer (EBL) or hold blocking layer (HBL) can be further added. At least one layer of graphene can be inserted between organic layers including the two electrodes.

In this case, there is an advantage in that an upper layer is formed on a lower layer whose surface is protected with graphene in the organic electronic device, by a solution process. Additionally, application and print processes can be performed after positioning graphene, and functions of display, circuit, battery, sensor, etc. can be integrated on a flexible plastic substrate.

Non-limiting examples of the organic electronic device are organic TFT, OLED, organic memory, organic semiconductor, organic solar cell, etc. With respect to the organic electronic device material, an inorganic material such as a semiconductor such as silicon and GaAs; a metal for wiring; and silicon oxide film and nitride film can be substituted with an organic material. A conductive polymer using a conjugated polymer material having a structure in which double and single bonds of carbons are alternated exhibits properties of metals, and thus has potential as wiring. In case of a semiconductor, due to an improvement in its material and process, a device having at least 1 $cm^2/Vs$ of mobility can be prepared using a small molecule such as pentacene. Additionally, as organic polymer can be used as various polymer insulating films, wiring, semiconductor, insulating film required for the electronic device can all be constituted as an organic material. The organic electronic device can be prepared without using a vacuum device used in existing semiconductor process. For example, an inexpensive plastic electronic component having a large area can be prepared by an inkjet printing. The organic electronic devices can be applied to a plastic-based electronic device in combination with a material that can be partially inked, rather than replacing all devices with organic materials.

Meanwhile, an organic semiconductor material transports a particular charge with high mobility according to which a functional group of the material molecule has a better property of either electron accepting or hole accepting. The material can be divided into electron transport type (n-type) or hole transport type (p-type) according to a type of the transported charge. According to intrinsic material properties that the organic semiconductor material possesses, a material with a good light-emitting property is mainly used for a light emitting layer of an OLED, and that with excellent thin film crystallinity and intermolecular packing properties is used as an active layer of an organic TFT. Additionally, a material with an excellent light absorbing property can be used for manufacturing an organic solar cell.

Advantageous Effect

According to the present invention, by using graphene which inhibits oxygen diffusion without blocking electron delivery, a technique preparing a desired material by a catalytic reaction on a graphene surface can be obtained, as well as a technique modifying the surface of the graphene which is chemically stable and thus does not generally cause a chemical reaction. Further, an element having the modified graphene can be applied to the display, semiconductor, and energy industries.

DESCRIPTION OF DRAWINGS

FIG. 1 is a schematic diagram of the surface modification using chemical reaction transparency of graphene according to the present invention.

FIG. 2 is a flow chart showing the process of the surface modification using chemical reaction transparency of graphene according to the present invention.

FIG. 3 is a schematic diagram of a layered structure, which can be provided by the method of modifying the graphene surface according to an exemplary embodiment of the present invention, including a first layer (material A) including various catalysts; a second layer comprising graphene formed on the first layer; and a product (material B) formed by the catalytic reaction on the second layer surface.

FIG. 4 is a schematic diagram of a layered structure, which can be provided by the method of modifying the graphene surface according to an exemplary embodiment of the present invention, including a support layer; a first layer including a catalyst formed on the support layer; a second layer comprising graphene formed on the first layer; and a product formed by a catalytic reaction on the second layer. The support layer and the catalyst are $SiO_2/Si$ and ZnO, respectively, and a ZnO nanorod is formed as the product of the catalytic reaction.

FIG. 7 is an image of a hydrogen sensor in which the graphene prepared according to an exemplary embodiment of the present invention and platinum nanoparticles formed on the surface of the graphene, and a hydrogen sensing result.

FIG. 8 shows cell growths on a glass on which graphene is transferred and that on which polylysine is laid and graphene is transferred thereon.

BEST MODE

Hereinafter, the present invention will be described in further detail with reference to exemplary embodiments. These exemplary embodiments are for illustrative purposes only and are not to be construed as limiting the scope of the present invention.

Example 1: Modification of Graphene Surface Using Chemical Reaction Transparency As a substrate for positioning graphene, a copper foil (46986, 99.8% metal basis, Alfa Aesar) of 0.25 μm thickness×6 cm width×6 cm length was prepared. As a method for forming a graphene layer, chemical vapor deposition (CVD) was used to position a graphene layer on one side of a copper foil layer.

For the transfer, polymethyl methacrylate (PMMA), a polymer capable of supporting the graphene layer, was spin-coated on the positioned graphene layer at room temperature for 30 seconds at 2000 rpm using a spin coater (Midas System). A copper etching solution (Transene) was used to dissolve the copper foil. The graphene was transferred on various first material layers, and PMMA, the polymer for support, was removed by dissolving with acetone. For the first material layers, Ge, Al, Al patterned on the $SiO_2$ layer, Si, GaAs, and Cu were used.

As described above, the top surface of the graphene layer transferred on the first material layers was in contact with a 0.1 mM $HAuCl_4$ aqueous solution, i.e., a condition where Au can be extracted, for 3 minutes and was then removed therefrom. In other words, by using $HAuCl_4$ as a second material, a third material layer, i.e., Au layer, was formed.

Figure 5:
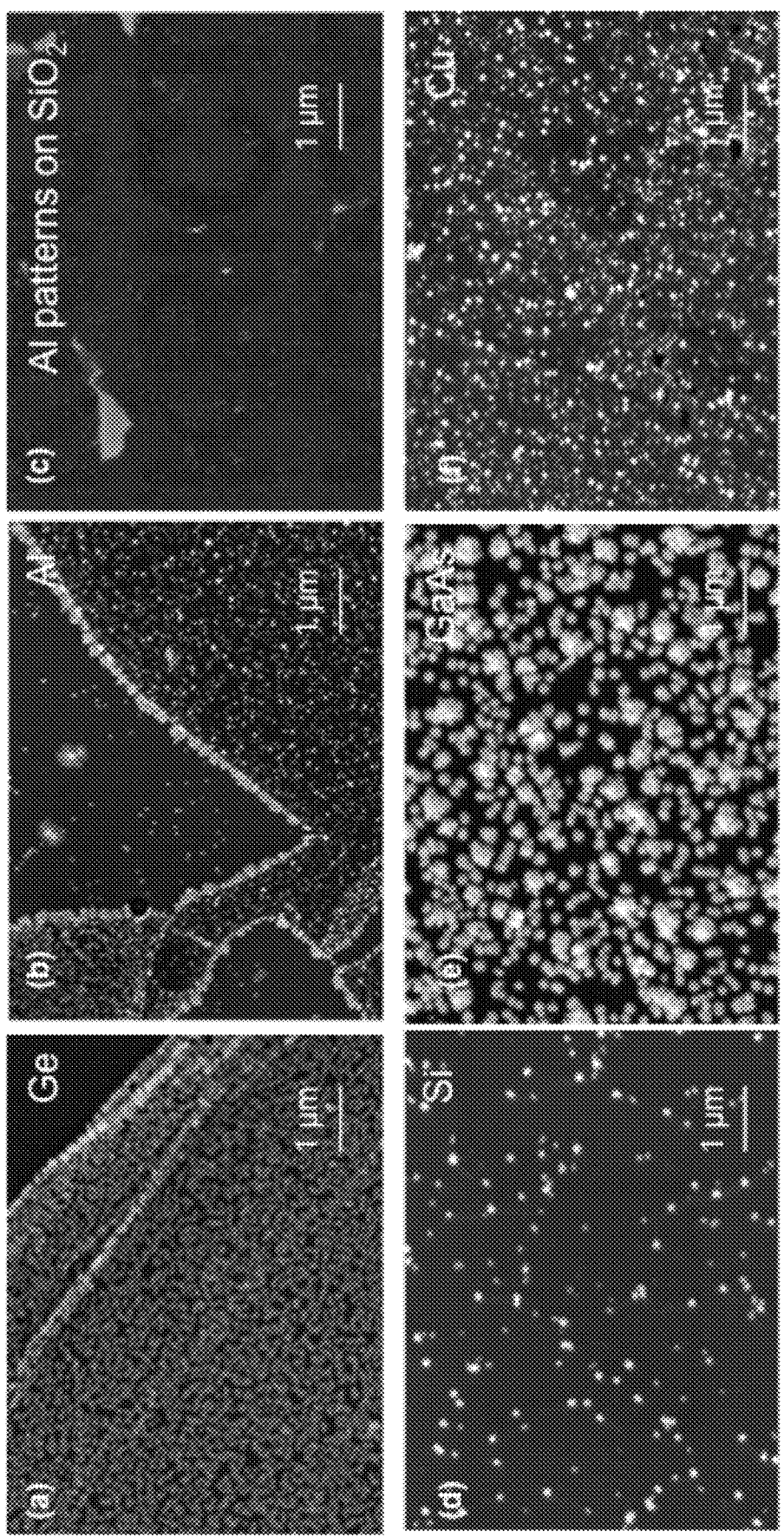
FIG. 5 is an electron micrograph of the layered structure which can be provided by the graphene surface modification method according to Example 1 of the present invention. Ge, Al, Al patterned on the $SiO_2$ layer, Si, GaAs, and Cu are used as a catalyst in (a), (b), (c), (d), (e), and (f), respectively.

As a result of investigating the modified graphene surface via an electron microscope, there were Au nanoparticles of the third material layer formed on the graphene surface, as shown in FIG. 5.

Example 2: Modification of Graphene Surface Using Chemical Reaction Transparency As a substrate for positioning graphene, a copper foil (46986, 99.8% metal basis, Alfa Aesar) of 0.25 μm thickness×6 cm width×6 cm length was prepared. As a method for forming a graphene layer, chemical vapor deposition (CVD) was used to position a graphene layer on one side of the copper foil layer.

For the transfer, polymethyl methacrylate (PMMA), a polymer capable of supporting the graphene layer, was spin-coated on the positioned graphene layer at room temperature for 30 seconds at 2000 rpm using a spin coater (Midas System). A copper etching solution (Transene) was used to dissolve the copper foil. The graphene was transferred on ZnO, the first material layer which is patterned on $SiO_2/Si$, the support layer, as shown in FIG. 4, and PMMA, the polymer for support, was then removed by dissolving with acetone.

The graphene layer transferred on the first material layer as described above was reacted hydrothermally in 2.5 mM $Zn(NH_3)_2$ and hexamethylenetetramine (HMTA) solution, i.e., a condition in which ZnO nanorod can grow, at 80° C.

for an hour. That is, using Zn(NH$_3$)$_2$ as a second material, the ZnO layer (third material layer) was formed in a nanorod form.

Figure 6:
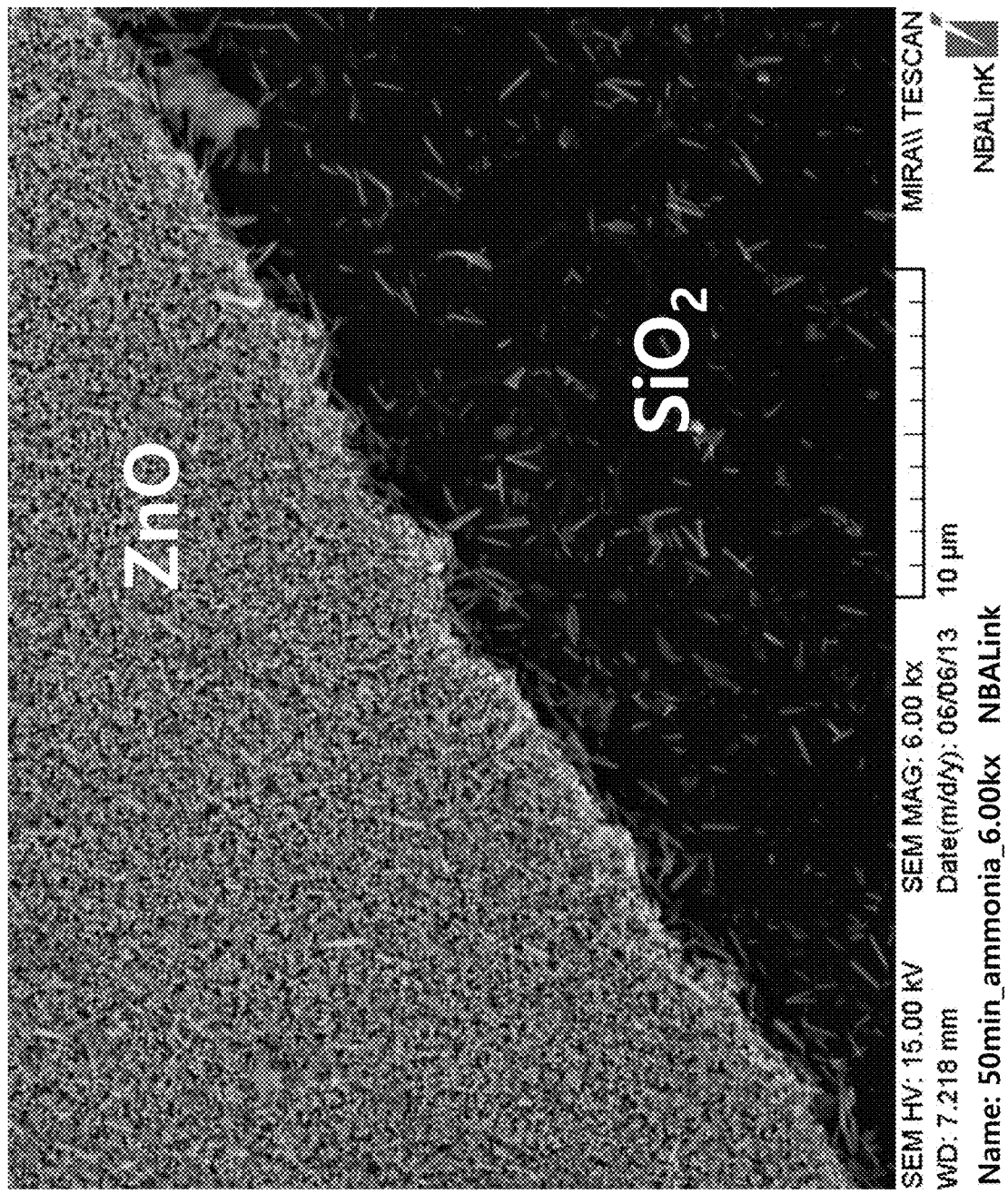
FIG. 6 is an electron micrograph of the structure which can be provided by the graphene surface modification method according to Example 2 of the present invention.

As a result of investigating the modified graphene surface via an electron microscope, there were ZnO nanorods formed on the graphene surface, as shown in FIG. 6. Here, produced ZnO nanorods has a matching atomic arrangement with the bottom ZnO substrate underneath graphene, transparency of graphene enables the growth of epitaxial material.

Example 3: Modification of Graphene Surface on an Element Surface

Based on commercially available graphene sensor device as a device which requires a graphene layer, whether the sensor device can be manufactured by applying the method of modifying the graphene surface of the present invention was tested.

As the result shown in FIG. 7, the platinum nanoparticles were formed on the graphene surface using graphene transparency. It was confirmed that the platinum nanoparticles dissociate hydrogen molecules to hydrogen atoms, and provide electrons to the graphene surface, thereby causing a change in current, so that the modified graphene surface can be used as a hydrogen sensor.

Example 4: Preparation of a Sensor which Uses Surface Plasmon Resonance (SPR) of Gold Nanoparticles-Modified Graphene Using the transparency of graphene, gold nanoparticles were formed on the graphene surface as in Example 1. The gold nanoparticles were formed in a relatively consistent size on the graphene surface in a high density, and could be used as a transparent SPR sensor.

Example 5: Experimentation on Cell Growth Using Graphene Transparency

A cell can grow on a metal surface using the transparency of graphene. Generally, the metal surface is not appropriate for a cell to be adsorbed thereonto and grow thereon, and thus undergoes a modification process. In the exemplary embodiments of the present invention, polylysine, as a material enabling the cells to be well adsorbed onto the metal surface, was functionalized, and graphene was transferred, followed by a cell culture experiment. As a result, it was confirmed that the feature of electron transfer of metal was maintained, while growing the cells on the metal surface using the graphene layer as a intermediary.

Additionally, in a case of using glass instead of the metal, cell growth can be promoted using the transparency of graphene. Specifically, an experiment on cell growth was conducted on the graphene surface transferred on glass, and on glass on which polylysine is laid and graphene is transferred. The result thereof is shown in FIG. 8. As shown in FIG. 8, it was confirmed that cell growth was more promoted on the substrate where polylysine is laid under graphene.

The invention claimed is:

1. A method of performing a catalytic reaction using chemical transparency of graphene on a substrate comprising the steps of:
   providing a catalyst disposed on a portion of a first layer to form a catalyst layer comprising one or more catalytic regions and one or more non-catalytic regions; and a graphene layer covering the one or more catalytic regions and the one or more non-catalytic regions;
   contacting a reactant with the graphene layer; and
   reacting the reactant with the catalyst at the one or more catalytic regions through the graphene layer so that the catalytic reaction occurs on the graphene layer along the catalyst pattern, wherein the one or more non-catalytic regions may be provided in the edge of the one or more catalytic regions so that the catalyst and the reactant does not directly contact.

2. The method of claim 1, wherein the catalyst is a photocatalyst, an electrocatalyst, or an electrode active material.

3. The method of claim 1, wherein the catalyst act as a reducing agent in the catalytic reaction.

4. The method of claim 1, wherein the graphene layer inhibits inactivation of the catalyst.

5. A method of preparing a surface-modified graphene through a catalytic chemical reaction on a substrate comprising a catalyst disposed on a portion of a first layer to form a catalyst layer comprising one or more catalytic regions and one or more non-catalytic regions; and a graphene layer covering the one or more catalytic regions and the one or more non-catalytic regions
   contacting a reactant with the graphene layer; and
   performing a catalytic chemical reaction of the reactant with the catalyst at the one or more catalytic regions through the graphene layer so that the catalytic reaction occurs on the graphene layer along the catalyst pattern, wherein the one or more non-catalytic regions may be provided in the edge of the one or more catalytic regions so that the catalyst and the reactant does not directly contact.

6. The method of claim 5, wherein the one or more catalytic regions and the one or more non-catalytic regions forms a catalyst pattern, and the catalytic chemical reaction is performed at the catalyst where the graphene layer is positioned on the one or more catalytic regions, thereby preparing the surface-modified graphene along the catalyst pattern.

* * * * *